United States Patent [19]

von Weissenfluh

[11] 4,449,928
[45] May 22, 1984

[54] UNIVERSAL CERVICAL MATRIX FOR DENTAL USE

[75] Inventor: Beat von Weissenfluh, Gentilino, Switzerland

[73] Assignee: Hawe-Neos Dental Dr. H. v. Weissenfluh SA, Gentilino, Switzerland

[21] Appl. No.: 426,184

[22] Filed: Sep. 28, 1982

[30] Foreign Application Priority Data

Nov. 9, 1981 [CH] Switzerland ............... 7334/81

[51] Int. Cl.$^3$ ............................................. A61C 9/00
[52] U.S. Cl. ........................................ 433/40; 433/229
[58] Field of Search .................. 433/39, 40, 228, 229

[56] References Cited

U.S. PATENT DOCUMENTS

| | | | |
|---|---|---|---|
| 2,603,871 | 7/1952 | Call | 433/90 |
| 3,628,249 | 12/1971 | Wurl | 433/80 |

FOREIGN PATENT DOCUMENTS

| | | | |
|---|---|---|---|
| 152841 | 2/1903 | Fed. Rep. of Germany | 433/80 |
| 2130068 | 11/1972 | France | 433/80 |
| 294164 | 1/1954 | Switzerland | 433/80 |
| 626247 | 11/1981 | Switzerland | 433/228 |

*Primary Examiner*—Robert Peshock
*Attorney, Agent, or Firm*—Young & Thompson

[57] ABSTRACT

The cervical matrix in question is universal as each exemplar is suitable to be applied to a considerable number of teeth of different shape, therefore few ranges of matrices of different curvature (for incisor, canine and molar teeth of adults and children) suffice to cope with all the requirements. The matrix has a lamina (1) transparent to ultraviolet and luminous rays curved with a radius of curvature (r) less than that of the teeth to which it is applied. To the lamina is fixed a stem (2) which permits of grasping it with the forceps and pressing it against the tooth subjecting for a few seconds the whole to ultraviolet or visible irradiations to effect the beginning of the process of polymerization of the filling material after which the matrix is detached and the polymerization continued.

5 Claims, 9 Drawing Figures

UNIVERSAL CERVICAL MATRIX FOR DENTAL USE

The present invention has as its object a universal cervical matrix for dental use transparent to ultraviolet rays and to the rays of the visible spectrum to permit rapid hardening by polymerization of the filling material and of material which does not adhere to that of the said filling.

Cervical matrices for dental use are already known, transparent to ultraviolet rays and to the rays of the visible spectrum, of material which does not adhere to that of the filling, each characterized by a transparent plate preferably made of plastic material, bent to adhere perfectly to the shape of the tooth in course of filling. After introduction into the cavity of the tooth, of the filling material, and the matrix is applied while holding it for some time with a forceps and causing the matrix to be passed through by a beam of ultraviolet or luminous rays for a few seconds, the polymerization process of the filling material starts, which permits of removing the matrix and of continuing the irradiation until complete hardening takes place (see in this respect Swiss Pat. No. 626,247). The drawback presented by the above described matrix consists in that for each shape of tooth a special matrix having the complementary shape or proximate to that of the said tooth is required due to which the dentist must have available a very considerable number of matrices to be able to adapt them to every shape of tooth.

The matrix according to the present invention differs from that described above the fact that it is universal, that is, it is adapted to a great diversity of shapes of teeth, so that with a limited range of matrices the dentist can meet all the demands that is, adapt them to the shape of incisors, canine teeth, and molar teeth of adults and children.

It is characterized by a concave elastic lamina with a radius of curvature less than that of the different teeth to which it can be applied and thinned at the end to be able to penetrate under the gum, the lamina being provided at the rear with a stem in order to be able to grasp it with forceps and press it strongly against the tooth to be treated so that by increasing its radius of curvature it can be adapted perfectly to the shape of the tooth to which it is applied.

An object of the present invention is also the method for using the matrix in question, a method which will be explained later.

The attached drawing shows three preferred non-limiting embodiments of the matrix in question adaptable to various types of teeth.

Figure 1:
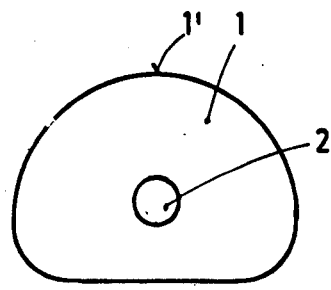
FIG. 1 shows in elevational view a first embodiment for molar teeth.
Figure 2:
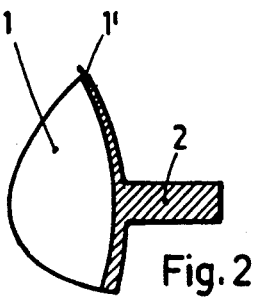
FIG. 2 shows it in cross section and FIG. 3 shows it in plan view from above.
Figure 3:
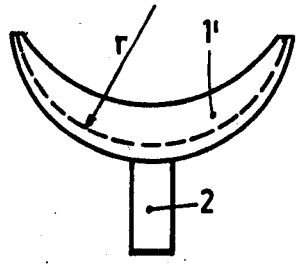
Figures 4, 5:
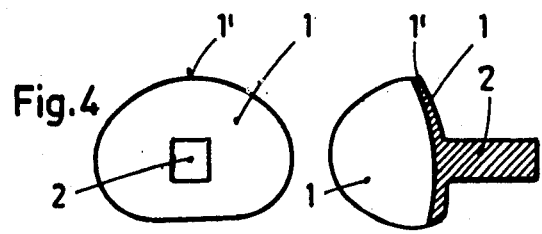
FIG. 4 shows a second embodiment much smaller and rounded with a stem of square section for incisor teeth.
FIG. 5 shows the cross section of the matrix of FIG. 4.
Figure 6:
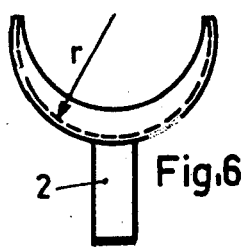
FIG. 6 is the plan view of same.
Figure 7:
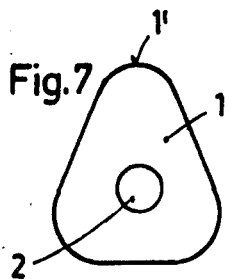
FIG. 7 shows a further triangular embodiment with rounded vertices for canine teeth.
Figure 8:
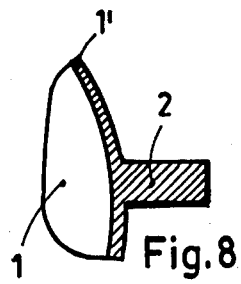
FIG. 8 is the corresponding cross section.
Figure 9:
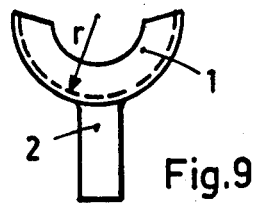
FIG. 9 is the plan view from above.

Refering to the various figures, the matrix consists of a lamina 1 of elastic transparent material preferably made of thermoplastic synthetic resin permeable to ultraviolet rays and to the visible rays of the spectrum and concave with a radius of curvature "r" less than that of the various teeth to which it may be applied so that when the stem 2 is grasped with forceps and the lamina is pressed against the tooth to be treated, increasing its radius of curvature, it assumes perfectly the shape of the said tooth whichever it may be.

Of special importance is the fact that the end of the lamina is thinned in order to be able to penetrate easily under the gum when the filling material extends under the said gum.

Taking into consideration the considerable difference in shape between the incisor, canine and molar teeth of an adult and of a child it will be understood immediately how not having available a universal matrix like the subject of the present invention, the dentist is compelled to have recourse to a considerable number of matrices of conventional type whilst with the matrix according to the present invention a few series of different sizes and shapes such as these illustrated in the various figures suffice for him to cope with every requirement.

The method for applying the matrix in question to the toth during a filling is as follows:

After having introduced into the cavity of the tooth the filling material hardenable by polymerization under the ation of ultraviolet rays or the visible light of the spectrum there is applied onto the tooth the matrix according to the present invention pressing it strongly against the tooth by means of the forceps which holds it by its stem so that the matrix assumes perfectly the shape of the tooth. There is then caused to pass ultraviolet or luminous radiation through the matrix holding it always by its stem until the beginning of the polymerization of the filling material and when this material is sufficiently hardened the matrix is removed and the irradiation is continued until complete polymerization.

As synthetic resins for realizing the matrix in question are selected those which do not adhere to the filling material and which are transparent to the aforesaid radiations.

The resin constituted by polymeric methyl pentene is especially suitable for the purpose.

It is possible for better grasping of the stem 2 of the matrix to make a special forceps the jaws of which in agreement with the end which grasps the stem are formed according to the shape of the said stem to facilitate the grasping.

A possible articulation in the proximity of the ends of the forceps may facilitate the adaptation of the matrix to the tooth to be treated.

It is possible for the shape and the material of the matrix in question to be capable of being of any kind adapted to the various requirements without departing from the scope of protection of the patent.

I claim:

1. A universal cervical matrix for dental use transparent to ultraviolet rays and to rays of the visible spectrum to permit rapid hardening by polymerization of the filling material and of a material which does not adhere to that of the said filling, characterized by a concave elastic lamina (1) with radius of curvature (r) less than that of the various teeth to which it may be applied and tapered to thin edges (1') to be able to penetrate under the gum, the lamina being provided at the rear with a stem (2) adapted to be grasped with forceps so as to press it strongly against the tooth to be treated so that by thus increasing its radius of curvature it can be adapted perfectly to the shape of the tooth to which it is applied.

2. A matrix according to claim 1, characterized in that to permit of the filling of teeth of many diverse shapes there is provided a series of matrices each series of which has a radius of curvature different from that of the other series.

3. A matrix according to claim 1, characterized in that it is made of synthetic resins which do not adhere to the filling material.

4. A matrix according to claim 3, characterized in that it is made of polymer of methylpentene.

5. A method for filling a tooth, comprising introducing into the cavity of a tooth a filling material hardenable by polymerization under the action of ultraviolet rays or visible light of the spectrum, then applying against the tooth to cover the filling material a matrix that is transparent to ultraviolet rays and to rays of the visible spectrum, the matrix being a concave elastic lamina whose radius of curvature is less than that of the tooth surface to which it is applied and which has a stem protruding outwardly from the convex side of the lamina, grasping the stem with forceps and pressing via the forceps the lamina against the tooth until the lamina assumes perfectly the shape of the tooth, exposing the filling material to ultraviolet or luminous radiation that passes through the matrix while holding the stem with the forceps until the beginning of polymerization of the filling material, and when the filling material is sufficiently hardened, removing the matrix and continuing the irradiation until the filling material has completely polymerized.

* * * * *